United States Patent [19]

McRae

[11] Patent Number: Plant 5,922

[45] Date of Patent: Mar. 31, 1987

[54] LILY PLANT NAMED PIXIE FLAME

[75] Inventor: Edward A. McRae, Boring, Oreg.

[73] Assignee: Melridge Inc., Sandy, Oreg.

[21] Appl. No.: 659,239

[22] Filed: Oct. 9, 1984

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Chas. W. Rummler; John B. Lungmus

[57] ABSTRACT

A new hybrid Asiatic lily cultivar particularly distinguished by the orange red and golden orange coloring of the tepals of its medium sized blooms and by its very bushy and lush foliage borne on a single erect stem which bears a large number of buds and flowers.

2 Drawing Figures

BACKGROUND OF THE INVENTION

This new variety of lily plant originated as a seedling resulting from the crossing of an unpatented clone of "Byam's Ruby"×"Golden Chalice", as the seed parent, with "Red Carpet" (unpatented) as the pollen parent, which was done by me at Sandy, Oreg., with the object of producing new Asiatic lilies having improved flower color, a vigorous and strong plant habit, and a growth habit genetically short enough for pot culture without chemical treatment. This particular seedling was selected for propagation because of its very unusual coloration and its apparent vigorous, strong and upright growth habit, and asexual propagation was done by me and under my direction through several successive generations at Sandy, Oreg., by means of bulb scales, bulblets and division, the successive generations demonstrating that the novel and distinctive characteristics of the parent plant hold true from generation to generation and appear to be firmly fixed.

DESCRIPTION OF THE DRAWING

This Asiatic lily cultivar is illustrated in the accompanying photographic drawing which, in the upper portion, shows a face view of a fully opened flower, and in the lower portion the view illustrates a potted arrangement of stems showing flowers, bulbs and foliage of the new variety, both views being partially hand painted on black-and-white prints in order to show the true colors of the new flowers.

DESCRIPTION OF THE NEW PLANT

The following is a detailed description of my new Asiatic hybrid lily cultivar with color designations according to The R.H.S. Colour Chart of The Royal Horticultural Society at London, England, and with nomenclature according to The International Lily Register (Royal Horticultural Society, London, England, 2nd edition, 1969).

THE PLANT

Origin: Seedling

Parentage:

*Seed parent.*—A clone of Byam's Ruby×Golden Chalice, the seed parent being unpatented.

*Pollen parent.*—Red Carpet (unpatented).

Classification:

*Botanic.*—Hybrid Asiatic lily cultivar; Division 1-A of the Horticultural Classification of Lilies of The Royal Horticultural Society of London, England.

*Commercial.*—Asiatic lily hybrid.

Form: A relatively short, erect and very bushy single stem.

Height: 35 to 42 cm. from bulbs 12 to 14 cm. in circumference.

Growth: Very vigorous and upright with excellent strength.

Foliage:

*Quantity.*—Abundant.

*Size of Leaf.*—About 7 cm. long.

*Shape of leaf.*—Ensiform with acuminate tip.

*Texture.*—Leathery.

*Aspect.*—Glossy.

*Color.*—Both upper and under sides, medium green.

Bulbs:

*Size.*—Various, ranging up to 30 cm. in circumference.

*Color.*—White.

THE BUD

Form: Obtuse, long and urn-shaped.

Size: About 5 to 6 cm. long and about 5 cm. in circumference at maturity.

Number of buds: 4 to 7 per stem from a bulb of 12 to 14 cm. in circumference.

Opening rate: The bud opens slowly.

Color: When tepals first divide and when they begin to unfurl, brilliant bicolor orange/red.

Peduncle: Erect and about 2 to 5 cm. long.

*Color.*—Dark green with orange tinge.

THE FLOWER

Blooming habit: Annually recurrent, blooming once and profusely in midseason.

Size: Medium, about 15 cm. in diameter.

Borne: In clusters, from 4 to 7 on a single stem from a bulb 12 to 14 cm. in circumference.

Shape: Chalice shaped with tepals turning flatly outward and slightly reflexing.

Size:

*Tepals.*—About 8 cm. long and 2.75 to 3.75 cm. wide with slightly ruffled margins.

Appearance: The aspect is shiny.

Color: The margins and about the outermost third of the tepals are of a warm red, RHS. 33A-B; the nectary area is red and just above the nectary, there is a blotch of golden orange, RHS 25A, about 2 to 3 cm. wide and extending outwardly for about one-half to two-thirds the length of the tepal.

Spotting: A few tiny papillae are found just about the nectary furrow.

Pedicel on the newly opened flower:

*Length.*—About 4 to 9 cm.

*Color.*—Medium green.

*Form.*—The pedicel is sturdy and upright.

Persistence: The tepals stay on the stem for about three weeks, both on the plant and as a potted subject.

Fragrance: The flower is not fragrant.

Disease resistance: The flower and plant are exceptionally resistant to disease, particularly to Fusarium and Botrytis, as observed where grown in Multnomah County, Oreg.

THE REPRODUCTIVE ORGANS

Stamens, anthers:

*Arrangement.*—Typical of Liliaceae.

Pollen:

*Color.*—Reddish gold.

Pistils: One in number, about 5 cm. long.

Stigma:

*Color.*—Reddish orange.

Ovaries: Typical of genus Lilium.

THE FRUIT

Shape: The fruit is ovoid.

Color at maturity: Soft brown.

Fertility: The fruit is fertile.

This new Asiatic hybrid lily cultivar most nearly resembles the variety "Red Carpet" (unpatented) but is distinguished from "Red Carpet" by its shorter forcing period, its high degree of disease resistance and virus tolerance, its shorter stature and suitability for pot culture, its longevity, and in particular by its brilliant bicolored flowers.

I claim:

1. A new and distinctive variety of hybrid Asiatic lily plant, substantially as herein shown and described, characterized by its relatively short height, its bushy and abundant foliage and in particular the brilliant orange/red color of the flowers when the plant is in full bloom.

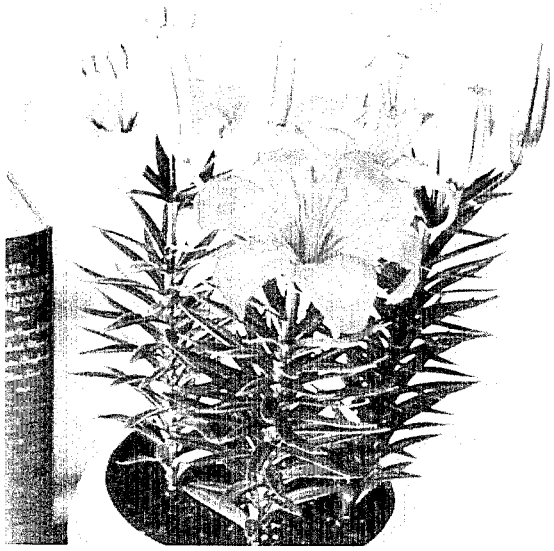
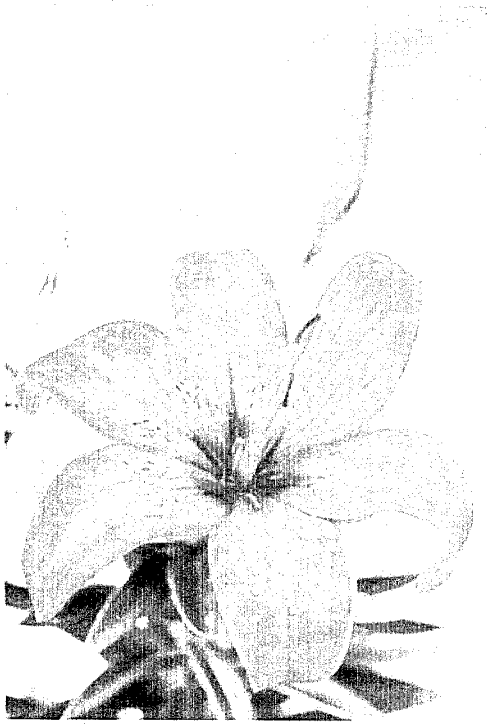

* * * * *